United States Patent [19]

Silva et al.

[11] Patent Number: 5,114,861
[45] Date of Patent: May 19, 1992

[54] DETECTING THE ENDPOINT IN INTERFACIAL AROMATIC POLYCARBONATE POLYMERIZATION REACTIONS

[75] Inventors: James M. Silva, Clifton Park; Thomas J. Fyvie, Schenectady, both of N.Y.

[73] Assignee: General Electric Company, Schenectady, N.Y.

[21] Appl. No.: 582,317

[22] Filed: Sep. 14, 1990

[51] Int. Cl.[5] .................... G01N 33/44; G01N 21/62
[52] U.S. Cl. ....................................... 436/85; 436/171
[58] Field of Search ................................ 436/85, 171

[56] References Cited

U.S. PATENT DOCUMENTS

| 4,378,454 | 3/1983 | Dick et al. | 526/59 |
| 4,506,867 | 3/1985 | Burzminski | 528/196 |
| 4,814,420 | 3/1989 | Brunelle et al. | 528/198 |

Primary Examiner—John W. Rollins
Attorney, Agent, or Firm—William H. Pittman; James C. Davis, Jr.

[57] ABSTRACT

A method is provided for detecting the endpoint of an interfacial aromatic polycarbonate polymerization reaction. The method involves illuminating a sample of the polymerization reaction mixture with a light source and monitoring the extent of apparent light scattering of the sample throughout the course of the polycondensation reaction until at the endpoint, a predetermined threshold extent of apparent light scattering is achieved.

20 Claims, No Drawings

DETECTING THE ENDPOINT IN INTERFACIAL AROMATIC POLYCARBONATE POLYMERIZATION REACTIONS

BACKGROUND OF THE INVENTION

This invention relates to a method of detecting the reaction endpoint in an interfacial aromatic polycarbonate polymerization reaction.

Organic polycarbonate polymers are useful plastics especially known for their excellent engineering properties and their inherent flame resistance. Organic polycarbonate polymers can be prepared directly by the reaction of phosgene with an organic bishydroxy compound, such as the aromatic bishydroxy compound 2,2-bis(4-hydroxyphenyl)propane, commonly referred to as bisphenol A. Alternatively, organic polycarbonate polymers can be prepared by polymerization of organic chloroformate oligomer mixtures. These oligomers comprise bischloroformates, monohydroxy monochloroformates and bishydroxy compounds which can be represented by the general formulas I, II, and III respectively hereinbelow:

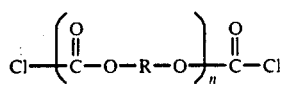
(I)

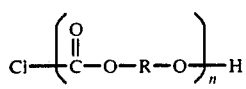
(II)

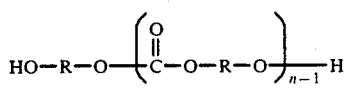
(III)

wherein R is a divalent $C_{6-30}$ aromatic radical and n is at least 1 and the number average for n is preferably less than 10. Low molecular weight ($n \leq 5$) organic chloroformate oligomers are especially useful in the preparation of cyclic polycarbonate oligomers which may be converted to very high molecular weight polycarbonates.

For a variety of reasons it is desirable to know the stoichiometric endpoint of aromatic polycarbonate polymerization reactions such as those described hereinabove. In direct phosgenations to make capped polymer the use of too little phosgene results in unreacted hydroxyl endgroups. The resulting polymer possesses an undesirably low molecular weight, and the polymer's properties, especially impact strength, are compromised. At the other end, the use of too much phosgene results in wasted time and raw material, while the polymer produced may also be degraded. In the polymerization of chloroformate oligomers, dropping a batch too soon results in unreacted chloroformate or hydroxyl endgroups. The chloroformate tends to be corrosive, and the resulting polymer may possess an undesirably low molecular weight and impact strength. Dropping a batch too late also wastes time and degrades product. In some instances, a chloroformate polymerization reaction requires additional phosgene for completion, and it is desirable to know the quantity of phosgene needed.

Several methods are known for detecting the stoichiometric endpoint of an organic polycarbonate polymerization preparation. U.S. Pat. No. 4,814,420 discloses a method comprising monitoring the rate of heat generated by the polymerization reaction mixture per unit of phosgene consumed, until at the stoichiometric endpoint of the reaction a rapid rise in heat is detected. The rapid rise in heat is related to the hydrolysis of excess phosgene in the reaction mixture. Disadvantageously, this method detects excess phosgene, and therefore is responsive only after the actual endpoint of the reaction is achieved. Moreover, this method is limited to direct phosgenation reactions, and is not applicable to detecting the endpoint of chloroformate oligomer polymerizations.

U.S. Pat. No. 4,506,067 teaches a method for detecting the stoichiometric endpoint of an aromatic polycarbonate resin preparation comprising detecting an increase of phosgene gas occurring in the vapor phase portion of the reactor at or shortly after the stoichiometric endpoint of the reaction. Several detection methods are disclosed including passing the overhead vapors through a water stream and measuring the resulting pH. Since phosgene hydrolyzes to yield hydrochloric acid, the pH of the water stream drops at or shortly after the endpoint of the reaction. Alternatively, the overhead vapors can be monitored by infrared spectroscopy for a characteristic phosgene band at 850 cm$^{-1}$. Disadvantageously, this method is limited to direct phosgenation reactions and cannot be applied to chloroformate oligomer polymerization preparations. Moreover, this method is based upon the presence of an excess of phosgene, and is therefore sensitive only after the actual endpoint of the polymerization reaction.

U.S. Pat. No. 4,378,454 discloses a method of preparing polycarbonates from dihydric phenols and phosgene in homogeneous mixtures of pyridine and a halogenated solvent. It is taught that periodically a sample of the reaction is mixed with an organic solution of 4-(p-nitrobenzyl)pyridine indicator to monitor the stoichiometric endpoint of the reaction. Just beyond the endpoint excess phosgene reacts with the indicator to give a color change from colorless to yellow. Disadvantageously, this method employs a sampling technique which is time consuming. More disadvantageously, this method is limited to direct phosgenation reactions and cannot be applied to chloroformate oligomer polymerization preparations. Even more disadvantageously, this method cannot be employed in two-phase interfacial reaction systems, such as those described in detail hereinafter, because the pyridine-containing solvent and indicator catalyze the hydrolysis of phosgene, thereby precluding reaction of phosgene with the indicator.

It would be desirable to have an improved and accurate method of detecting the reaction endpoint of a direct interfacial polycarbonate phosgenation polymerization reaction. It would be especially valuable if such a detection method could also be applied to detecting the reaction endpoint of interfacial chloroformate polycarbonate polymerization reactions.

SUMMARY OF THE INVENTION

This invention is a method of detecting the endpoint of an interfacial polycarbonate polymerization reaction. The endpoint may be a stoichiometric endpoint or an off-stoichiometric endpoint. By "stoichiometric endpoint" is meant that point in the polymer preparation reaction wherein each equivalent of aromatic hydroxyl endgroup has been converted to carbonate by reaction with an equivalent of phosgene or chloroformate endgroup. By "off-stoichiometric endpoint" is meant that point in the polymer preparation reaction wherein a predetermined extent of reaction has been achieved. At this point a predetermined portion of the aromatic hydroxyl endgroups has been converted to carbonate, while the remaining portion of aromatic hydroxyl endgroups is left unreacted at a lower concentration than the starting concentration.

The method of this invention comprises illuminating a sample of an interfacial aromatic polycarbonate polymerization reaction mixture with electromagnetic radiation of a wavelength of at least about 300 nanometers, and monitoring the proportion of incident radiation which is absorbed and scattered by the reaction mixture during the course of the polycondensation reaction. At or about the endpoint of the reaction, a predetermined threshold proportion is achieved, said threshold proportion being described in detail hereinafter. The polycondensation reaction is conducted in a heterogeneous mixture comprising water, a substantially water-insoluble organic liquid, an organobishydroxy compound or organochloroformate oligomer, an acid acceptor, an effective amount of an interfacial polycarbonate condensation catalyst, and optionally a polycarbonate chainstopper and phosgene.

This method is advantageous in that it can be constructed to operate continuously on-stream, and therefore time-consuming sampling of the reaction mixture is avoided. Moreover, this method possesses the added advantage of being applicable to aromatic chloroformate polymerization reactions as well as the direct phosgene polymerization route. Even more advantageously, this method is sensitive to the disappearance of hydroxyl endgroups; therefore, this method is more likely than prior art methods to detect the actual stoichiometric endpoint of a polycarbonate polymerization preparation. A further advantage is that off-stoichiometric endpoints may be determined by the method of this invention. Off-stoichiometric endpoints are useful in preparing polycarbonates with a low but controlled level of hydroxyl functionality.

DETAILED DESCRIPTION OF THE INVENTION

In accordance with the invention there is provided a method of detecting the reaction endpoint of a polycarbonate polymerization reaction. The method is applicable to direct phosgenation processes wherein an organobishydroxy compound, such as bisphenol A, is reacted with phosgene in the presence of an interfacial polycarbonate condensation catalyst to yield a polycarbonate polymer. In a preferred embodiment, the method is applicable to the polymerization of aromatic chloroformate oligomers to yield aromatic polycarbonates.

The polycarbonate polymerization reaction, whether by the direct phosgene route or the chloroformate route, is usually conducted in a two-phase liquid reaction medium comprising an aqueous phase and a substantially water-insoluble organic phase. The aqueous phase also contains an acid acceptor, typically an alkali or alkaline earth metal hydroxide, which functions to neutralize hydrochloric acid formed during the polymerization process. Other components of the polymerization reaction include either an organobishydroxy compound or an organochloroformate oligomer. The organobishydroxy compound frequently exists substantially as a solid, because typically the compound is not very soluble in either liquid phase. The organochloroformate oligomer is substantially solubilized in the liquid organic phase. An interfacial polycarbonate condensation catalyst, and optionally, a chainstopper are also employed, and these are usually partitioned between the two phases. If phosgene is employed, it is soluble in the liquid organic phase, as is the polycarbonate polymer. Although these reactions are commonly referred to as "interfacial", implying that the bulk of the reaction occurs in the interfacial region between the two liquid phases, it is possible that reaction also occurs in the bulk organic phase.

The organic solvent can be any organic liquid which solubilizes phosgene and the polycarbonate product, and is essentially insoluble in water. In addition, the solvent should be inert, that is, non-interfering with the phosgenation or chloroformate polymerization reaction. Especially suitable for use are the halogenated hydrocarbons, such as methylene chloride, chloroform, carbon tetrachloride, trichloroethylene, ethylene dichloride, chlorobenzene and the like, as well as aromatic hydrocarbons, such as benzene and toluene. Preferably, the organic solvent is methylene chloride. Water soluble solvents, such as pyridine, N,N-dimethylformamide, dioxane and tetrahydrofuran may also be employed provided that at least one water-insoluble solvent is also present in the reaction mixture, such that the resulting solvent-water mixture forms two distinct phases.

A wide variety of dihydroxy organic compounds may be employed in direct polymerization reactions with phosgene. Broadly, these compounds may be represented by the general formula:

$$R^2(OH)_x$$

wherein $R^2$ is an aromatic radical and x is at least 2. The sole reactive groups on these compounds are the hydroxyl moieties which provide reactive terminal protons.

The dihydroxy organic compounds of the above-identified formula which are dihydric phenols, that is, wherein x is 2 and $R^2$ is a divalent aromatic radical, are particularly preferred for polycarbonate synthesis. Some of these are represented by the general formula IV hereinbelow:

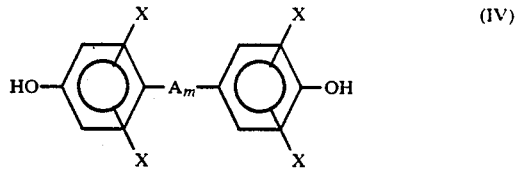

(IV)

wherein A is a divalent hydrocarbon radical containing 1-15 carbon atoms, or

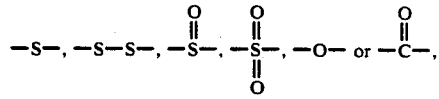

each X is independently hydrogen, chlorine, bromine, fluorine or a monovalent hydrocarbon radical such as an alkyl group of 1-4 carbons or an aryl group of 6-8 carbons such as phenyl, tolyl or xylyl and m is 0 or 1.

Suitable dihydroxy organic compounds include those disclosed by name or formula (generic or specific) in U.S. Pat. No. 4,217,438, the disclosure of which is incorporated by reference herein. In most instances, the preferred dihydroxy organic compound is 2,2-bis(4-hydroxyphenyl)propane, also known as bisphenol A. Another suitable compound is 6,6'-dihydroxy-3,3,3',3'-tetramethyl -1,1'-spiro(bis)indane.

It is, of course, possible to employ a mixture of two or more different dihydric phenols or a mixture of a dihydric phenol and an aliphatic alcohol in the direct phosgenation reactions suitable for the method of this invention. It is also possible to employ a copolymer of a dihydric phenol with a glycol or with a hydroxy-terminated polyester.

All of the dihydroxy organic compounds described in formula IV and by explicit nomenclature hereinabove are also useful in the synthesis of mixtures of organic chloroformate oligomers, the components of which are represented by the general formulas I-III, noted hereinbefore. The synthesis of chloroformate oligomers is achieved by reacting one of the above-identified organobishydroxy compounds with phosgene in a two-phase interfacial liquid medium under conditions such that the reaction proceeds only as far as the chloroformate oligomer mixture. Reaction conditions controlling the oligomerization include the concentration of the polycondensation catalyst, the pH of the aqueous phase, the temperature and the volume ratio of aqueous to organic phase, as described, for example, in U.S. Pat. No. 4,737,573, incorporated herein by reference. Generally, the catalyst concentration ranges from about 0 to about 0.2 mole per 100 moles bishydroxy aromatic compound; the pH set point ranges from about 2 to about 11; and the volume ratio of aqueous to organic phase at the conclusion of the phosgenation ranges from about 0.4:1 to about 1.0:1. Typically, the reaction temperature ranges from about 15° C. to about 50° C. It is frequently convenient to utilize methylene chloride and to operate at atmospheric pressure under refluxing methylene chloride conditions, which corresponds to a temperature of approximately 39° C.

In preparing polycarbonate polymers from a bishydroxy aromatic compound and phosgene directly or alternatively from an oligomeric carbonate chloroformate mixture, an interfacial polycarbonate condensation catalyst is employed, and is usually partitioned between both liquid phases. The catalyst can be any hydrogen halide acceptor commonly employed in interfacial polycarbonate condensation reactions, and is preferably a tertiary amine. Illustrative of well-known catalysts are the following: trimethylamine, triethylamine, allyldiethylamine, benzyldimethylamine, dimethylphenethylamine, N-methylpiperidine and the like. In addition to tertiary amines which are preferred, there also can be used as the catalyst quaternary salts, such as quaternary ammonium salts and quaternary phosphonium salts.

Any amount of condensation catalyst can be employed. However, generally, effective mole proportions relative to the hydroxy organic compound or chloroformate compound are within a range from about 0.025 mole percent to about 3.0 mole percent.

In addition to the condensation catalyst, optionally, a chainstopper such as monohydric phenol or substituted phenol can be employed to control the molecular weight of the polycarbonate polymer. There can be used from 0 to about 10 mole percent of chainstopper based on total moles of bisphenol in the mixture, and preferably from about 0.5 to about 6 mole percent.

The acid acceptor is typically any base which is capable of reacting with hydrogen halide formed during the polymerization reaction. Preferred are the alkali or alkaline earth metal oxides, hydroxides and carbonates, including lithium, sodium, potassium and calcium hydroxides, and sodium and potassium carbonates. More preferred are the lithium, sodium or potassium hydroxides, with sodium hydroxide being most preferred because of its availability and relatively low cost. The concentration of the acid acceptor solution is not critical and may range from about 0.2M to about 19M.

Optionally, the aromatic polycarbonate polymerization reaction may contain branching or crosslinking agents, for example, trifunctional phenols, such as tris(4-hydroxyphenyl)ethane, or trifunctional acid chlorides, such as trimellitic triacid chloride, such as are taught in U.S. Pat. No. 4,452,966. In addition, the reaction may contain minor amounts of aliphatic dicarboxylic acids, such as dodecanedioic acid, for the purpose of modifying the properties of the finished polycarbonate polymer.

The polymer preparation reaction can be conducted at any operable temperature and pH which yield the desired polycarbonate polymer. Generally, the reaction is conducted at a temperature in the range from about 0° C. to about 100° C., and preferably from about 25° C. to about 50° C. The pH of the aqueous phase is generally maintained in excess of 9. Preferably, the pH is maintained in the range from about 9.5 to about 13, and more preferably from about 10.0 to about 11.5.

The polymerization reaction mixture should be agitated, for example, by stirring. Alternatively, the reaction mixture may be pumped through motionless or static mixers in order to disperse one phase in the other.

According to the method of this invention, the endpoint of the polycarbonate polymerization reaction is determined by monitoring the proportion of incident electromagnetic radiation which is absorbed and scattered by said mixture. (The term "incident", as used herein, designates radiation passed into the mixture by the radiation source.) This proportion is sometimes identified hereinafter as extent of apparent light scattering ("ALS"). The ALS of the heterogeneous reaction mixture is monitored throughout the course of the polymer preparation reaction until a predetermined threshold ALS level is achieved at or near the endpoint.

Just after addition of the polycondensation catalyst to a mixture of oligomeric carbonate chloroformates when little, if any, polymerization has occurred, the two-phase reaction mixture appears milky white, and a beam of light is highly scattered. As the polymerization proceeds, the reaction mixture becomes clearer until at the stoichiometric endpoint, the reaction appears translucent, or nearly so. Accordingly, at the stoichiometric endpoint of the polymerization reaction, the ALS is significantly reduced compared with its value just after catalyst addition.

It is believed that the ALS of the polymerization medium is related to the concentration of unreacted aromatic hydroxyl endgroups. Without being bound or limited by such a theory, it is believed that the aromatic hydroxyl endgroups act as a surfactant which facilitates the creation of interfacial area and leads to a small droplet size of the dispersed phase. Thus, well before the reaction endpoint, when the aromatic hydroxyl moieties are at a high concentration, there is considerable surfactant, a high total interfacial area, and extensive scattering of the incident beam. As polymerization proceeds, hydroxyls are consumed. Thus, at the end of the reaction when there is essentially no hydroxyl remaining, there is also essentially no surfactant and therefore less interfacial area. Consequently, the droplets increase in size and the reaction mixture scatters less light.

In practice, a sample of the two-phase reaction mixture is illuminated in a sample cell with electromagnetic radiation and the output level from a light detector is monitored in order to infer the ALS for the sample. The detector response must be monotonically, but not necessarily linearly, related to the detected light intensity over a range of wavelengths.

For the purpose of this invention, the ALS is defined in terms of an apparent scattering coefficient. The intensity of light transmitted through the heterogeneous reaction mixture is attenuated according to Beer's law as modified for scattering samples:

$$I = I_0 \exp{-(\beta + \tau)x}$$

wherein
$I_0$ = intensity of incident light beam
$I$ = intensity of beam at distance x through the medium
$\beta$ = absorption coefficient
$\tau$ = scattering coefficient
$\beta + \tau$ = apparent scattering coefficient.

The incident beam is scattered by the immiscible droplets of the heterogeneous reaction mixture, which reduces the intensity of transmitted light relative to the intensity of the source. Absorption of the incident beam by the different molecular species, represented above by $\beta$, may also reduce the transmitted light intensity.

Although the definition of the apparent scattering coefficient suggests measuring transmitted light intensity, which is often preferred, it is also within the scope of the invention to detect scattered light intensity, i.e., the light intensity at one or more positions (or a range of positions or solid angle) that are not on a straight line path from the light source. The angular dependence of scattered light intensity has been developed in the prior art; reference is made, for example, to Mie, Ann. Physik, 25, 377 (1908). Thus, in principle it is possible to infer an ALS value from measurements of scattered light.

In the practice of this invention, it is not necessary to measure absolute ALS values. The measurement need only produce a value which is monotonically related to the intensity of detected light. Further, the detector output level (hereinafter sometimes "DOL") may either increase or decrease monotonically with the intensity of detected light. For example, for a detector measuring transmitted light, if the DOL increases monotonically with decreasing detected light intensity, it is monotonically directly related to the apparent scattering coefficient. Similarly, for a detector measuring scattered light, e.g., reflected light, if the DOL increases monotonically with decreasing detected light intensity, it is monotonically inversely related to the apparent scattering coefficient. For either type of relationship, the DOL may be used directly to establish the reaction endpoint.

Any light source is acceptable for the method of this invention provided that the wavelength range is such that the light scattering by the interfacial reaction mixture is sensitive to changes in the size of the liquid droplets and the absorption by molecular species is not excessive. Thus, any light source providing electromagnetic radiation of a wavelength greater than about 300 nanometers (nm) is suitable for the method of this invention. The wavelength bandwidth can be narrow or broad. Preferably, the light source has a wavelength in the range from about 300 nm to about 2,500 nm, which includes wavelengths in the near-ultraviolet across the visible through the near-infrared. More preferably, the light source has a wavelength in the range from about 350 nm to about 700 nm. Below the lowest preferred wavelength, there may be excessive absorption by the molecular species, which may interfere with the effect of droplet size on the extent of apparent light scattering, or there may be little effect of droplet size on the light scattering. Above about 2,500 nm, absorption by water and/or the organic solvent may interfere with the measurement. Acceptable light sources include Globars and Nernst glowers for the near-infrared; tungsten or tungsten-halide filament lamps, or the like, and hydrogen, deuterium, xenon, mercury and sodium arc discharges, argon-ion or other laser discharges, or fiber optic sources for the visible, near-ultraviolet or near infrared ranges. Preferably, the light source is a white light illuminator with a broad bandwidth in the visible range, such as a standard white light microscope illuminator.

A sample of the reaction mixture is placed in a sample cell which is illuminated with the light source. Any sample cell is suitable, provided that it transmits a sufficient portion of the incident beam. By this it is meant that the power of the incident beam or scattered light is not significantly reduced by the sample cell itself. Preferably, too, the sample cell is not water or solvent soluble. Suitable sample cells include quartz for the near IR, visible and ultraviolet or glass for the visible. Preferably, the sample cell is glass. In preferred embodiments the sample cell is built into a recirculation loop of a batch reactor or a continuous stirred tank reactor, or located at or near the end of a continuous flow reactor such as a pipe or plug flow reactor. These embodiments allow for continuous monitoring of the polymer preparation reaction and eliminate time consuming sampling techniques. Thus, the method of this invention is rapid and more accurate than prior art methods.

It is preferred to agitate the two-phase reaction mixture in the sample cell or in the reactor recirculation loop prior to circulation to the sample cell, so as to produce well-dispersed droplets.

The detector comprises any light-sensing means which is capable of converting the intensity of light signals into an electrical signal suitable for recording, such as on a strip chart recorder or display. Illustrative of suitable light-sensing means are photoconductive cells, photomultiplier tubes, photovoltaic cells, thermocouples, bolometers, Golay cells and the like. Preferably, the light-sensing means is a photoconductive cell which converts light signals into changes in resistance.

The location of the detector relative to the incident beam may vary. For example, the detector and the incident beam can be located along a straight line path on opposite sides of the sample cell. Such detectors would measure primarily transmitted light. Alternatively, the detector may measure primarily scattered light. Thus, the detector can be aligned at any angle relative to the incident beam, such as at a 90° angle or at a zero degree angle, in which case the detector would measure scattered light as reflected light. Preferably, the detector is located along a straight line path on the opposite side of the sample cell from the incident beam. Fiber optic cables may be used to conduct light from its source to the sample cell and/or to conduct light from the sample cell to the detector.

According to the method of this invention, the endpoint of the polycarbonate polymer preparation occurs when a predetermined ALS level is achieved. Because the DOL is monotonically related to the ALS, the endpoint of the reaction occurs when a predetermined DOL is achieved. This predetermined threshold DOL depends upon many parameters, including the specific reactants and organic solvent employed, the concentration of the reactants, the molecular weight of the polymer, the pH, the temperature and the amine catalyst level. It is necessary therefore to conduct a control reaction in order to determine the threshold DOL.

The control reaction is conducted employing all of the parameters, including specific reactants, solvents, concentrations, pH, temperature, percentage solids and the like, which are desired for the polymer preparation of interest. Throughout the course of the control reaction the DOL is continuously monitored and samples are periodically removed. Each sample is further analyzed to determine the concentration of the aromatic hydroxyl endgroup. Any analytical technique known to those skilled in the art for determining hydroxyl endgroup concentration is suitable for the method of this invention. The preferred method of analyzing for hydroxyl endgroup concentration is Fourier transform infrared (FTIR) spectroscopy, such as described in *Encyclopedia of Industrial Chemical Analysis*, Volume 27, Snell Hilton, eds., Interscience 1966, pp. 331, 332 and 339. Typically, this involves measuring the intensity, taken as peak height, of the aromatic hydroxyl peak at about 3,600 cm$^{-1}$.

A plot of DOL versus the measured aromatic hydroxyl concentration is then prepared. The predetermined threshold DOL is the value corresponding to the predetermined and desired aromatic hydroxyl concentration. This predetermined hydroxyl concentration may be finite or non-detectable. For example, at the stoichiometric reaction endpoint wherein essentially no aromatic hydroxyl endgroups are detected by FTIR spectroscopy, the DOL is at the stoichiometric threshold value. Alternatively, at an "off-stoichiometric" endpoint wherein the concentration of aromatic hydroxyl endgroups has decreased to a predetermined low level, the DOL is at the "off-stoichiometric" threshold value. In either case the threshold DOL is the target value for subsequent reactions under substantially identical conditions.

The data collected as described hereinabove is analyzed relatively easily with the help of a standard graph plotting the intensity of the infrared aromatic hydroxyl peak as a function of hydroxyl concentration. This graph is readily constructed by measuring the intensity of the infrared peak, taken as peak height, for a series of standard samples of organobishydroxy or organo chloroformate compounds of known aromatic hydroxyl concentration. Thereafter, the DOL measurements obtained from the control reaction, described hereinabove, can be correlated with aromatic hydroxyl concentration via the intensity of the infrared peak. As stated hereinbefore, the stoichiometric threshold DOL is the value which correlates with essentially zero or non-detectable aromatic hydroxyl concentration. Off-stoichiometric threshold DOL values correlate with predetermined low levels of unreacted aromatic hydroxyl endgroups.

It is apparent from the discussion hereinabove that the method of this invention has many advantages over the prior art. Since the method relies upon detection of the DOL which is related (through ALS) to unreacted aromatic hydroxyl endgroups, the method is applicable to polycarbonate preparations that directly employ phosgene as well as polymerizations of carbonate chloroformate oligomer mixtures. For the same reason, this method more accurately measures the stoichiometric endpoint than methods relying upon the detection of excess phosgene. In addition, for the same reason, this method may be applied to syntheses of off-stoichiometric polycarbonate polymers.

ILLUSTRATIVE EMBODIMENT

The following example is illustrative of the process of this invention; but is not intended to be limiting thereof.

EXAMPLE (A) Polymerization Reactor and ALS Measurement Equipment: A 1-liter reactor was fitted with a dual 2.5", six blade flat turbine agitator operating at 450 rpm., a condenser (20° F. coolant), a dip tube for addition of phosgene gas and a dip tube for the addition of sodium hydroxide. The reactor also contained a recirculation loop fitted with an electrode for measuring pH. The pH electrode controlled a pump which was set to deliver a 50 weight percent sodium hydroxide solution at a molar flow rate of about twice the molar phosgene flow rate. A clear glass flow cell (1" O.D.) was installed into the recirculation loop just downstream from a recirculation pump. A two-phase liquid reaction mixture, described hereinbelow, well dispersed by agitation in the reactor was continuously pumped through this cell. A light source comprising a standard incandescent laboratory illuminator (30 watts) shined white light onto the cell. A detector comprising a photoconductive cell (GE type A-35) was mounted on the opposite side of the flow cell from the light source. The electrical resistance of the detector depended upon the power of the incident light beam, measuring 650 $\Omega$ at 100 ft.-candles and 12,000 $\Omega$ at 2 ft.-candles. The photoconductive cell comprised part of a simple voltage divider circuit. Thus, the voltage drop across the photoconductive cell was proportional to the light absorbed by the flowing liquid. This voltage drop was taken to be the DOL and was recorded on a standard strip chart recorder.

(B) Preparation of Chloroformate Oligomers: The reactor described hereinabove was charged with bisphenol A, (BPA, 186 g; 0.816 mole), methylene chloride (550 ml.), deionized water (250 ml.), a 50 weight percent solution of sodium hydroxide (5 ml.) and triethylamine (0-0.05 mole percent based on BPA). Phosgene was metered into the reactor at a flow rate of 5.8 g./min. at a pH set point of 8.2. Sodium hydroxide was added on demand to maintain the pH set point. Whenever the pH fell below the set point, a 50 weight percent sodium hydroxide solution was pumped in at 6.7 ml./min. Otherwise, the sodium hydroxide flow rate was zero. Phosgenation was conducted for 15.75 minutes (1.14 mole COCl$_2$/mole BPA). The reaction product comprised mono- and bischloroformate oligomers and bishydroxy oligomers.

(C) Capping/Polymerization of Chloroformate Oligomers: After preparation of the chloroformate oligomers, described hereinabove, the reaction mixture was depleted of phosgene by stirring and recirculating for 4–5 minutes without further addition of sodium hydroxide. Phenol (3.45 g.; 0.0367 mole) was then added over a 2-4 minute period for the purpose of endcapping. Additional triethylamine catalyst was added to adjust the amine level to 50 ppm. relative to methylene chloride. After endcapping was completed, the pH set point was raised to 9.0 and sufficient triethylamine polycondensation catalyst was added over a 2-4 minute period to bring the total amine level to 0.5 mole percent based on BPA and to initiate polymerization. The pH point was raised to 10.5.

The DOL of the endcapping/polymerization reaction was monitored continuously and polymerization samples were taken: (1) just after addition of the amine catalyst, (2) at the end of polymerization when the pH leveled off and there was no further sodium hydroxide demand; and (3) at 1 minute after termination of a 1 minute rephosgenation. Rephosgenation was conducted at a pH set point of 10.5 and a phosgene flow rate of 5.8 g./min. The sodium hydroxide flow rate was 7.6 ml./min. when the pH was below set point and zero otherwise. The reaction samples were quenched in 3N HCl and washed once with deionized water. The organic phase was then dried, redissolved in dry methylene chloride and analyzed by Fourier transform infrared spectroscopy (FTIR) for residual aromatic hydroxyl content, by high pressure liquid chromatography and be gel permeation chromatography (GPC). The results are set forth in Table I.

TABLE I

| Sample[1] | Rephosgenation | DOL (mvolts) | FTIR (ppm.-OH) | GPC[2] $M_w$ (K) | $M_n$ (K) |
|---|---|---|---|---|---|
| 1-1 | — | 200 | >2000 | — | — |
| 1-2 | No | 149 | 40 | — | — |
| 1-3 | 1 | 135 | ND[4] | — | — |
| 2-1 | — | 285[3] | >2000 | — | — |
| 2-2 | No | 190 | 1330 | 17.0 | 7.4 |
| 2-3 | 1 | 160 | 25 | 17.5 | 7.5 |
| 2-4 | 2 | 150 | ND[4] | 17.5 | 7.6 |
| 3-1 | — | 285 | >2000 | — | — |
| 3-2 | No | 185 | 1440 | 16.4 | 6.7 |
| 3-3 | 1 | 150 | ND[4] | 18.4 | 7.3 |
| 3-4 | 2 | 145 | ND[4] | 18.7 | 7.6 |

[1]Samples #-1 were taken just after addition of amine catalyst. Samples #-2 were taken at end of polymerization when pH levelled off and there was no further NaOH demand. Rephosgenation samples #-3 and #-4 were taken one minute after COCl₂ was turned off.
[2]$M_w$ is weight average molecular weight and $M_n$ is number average molecular weight, as determined by gel permeation chromatography.
[3]Light source was moved between Sample 1-3 and Sample 2-1.
[4]ND means not detected.

It was observed that the DOL of the polymer preparation reaction was greatest just after addition of the amine catalyst, at Samples 1-1, 2-1 and 3-1. Simultaneously, the concentration of aromatic hydroxyl endgroup as determined by infrared spectroscopy was also greatest. At that point the appearance of the reaction was milky white. It was further seen that the DOL decreased significantly as a function of time to the end of the sodium hydroxide demand at Samples 1-2, 2-2 and 3-2. At this stage the aromatic hydroxyl concentration was reduced, but was still readily observable by FTIR. The DOL was also seen to decrease further with the first rephosgenation (Samples 1-3, 2-3 and 3-3). At this stage the aromatic hydroxyl was not detectable for Samples 1-3 and 3-3, and thus this stage determined the threshold DOL for those samples. In Sample 2-3 the aromatic hydroxyl peak was weak but still detectable. The DOL was then seen to decrease even further with the second rephosgenation (Samples 2-4 and 3-4). At this stage, aromatic hydroxyl was not detected for Samples 2-4 and 3-4, thus this stage determined the threshold DOL for those samples. On an average, a DOL of 150 millivolts was taken to be the predetermined stoichiometric threshold DOL for this polymer preparation reaction. Thus, the threshold DOL of 150 millivolts can be employed in essentially identical polycarbonate polymerization reactions to mark the stoichiometric endpoint of the reaction.

What is claimed is:

1. A method of detecting the endpoint of an interfacial aromatic polycarbonate polymerization reaction comprising illuminating a sample of the polymer preparation reaction mixture with electromagnetic radiation having a wavelength of at least about 300 nanometers, and monitoring the proportion of incident radiation which is absorbed and scattered by the reaction mixture during the course of the polycondensation reaction until at or about the endpoint of the reaction mixture a predetermined threshold proportion is achieved, wherein the polycarbonate polymerization reaction is a heterogeneous mixture comprising water, a substantially water-insoluble organic liquid, an organobishydroxy compound or organochloroformate oligomer, an acid acceptor, an effective amount of an interfacial polycarbonate condensation catalyst, and optionally a polycarbonate chainstopper and phosgene.

2. The method of claim 1 wherein the polycarbonate polymerization reaction mixture contains an organobishydroxy compound and phosgene.

3. The method of claim 2 wherein the organobishydroxy compound is represented by the formula

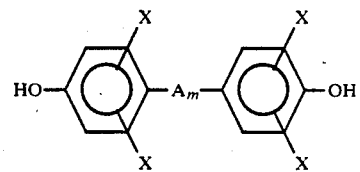

wherein A is a divalent hydrocarbon radical containing 1-15 carbon atoms, or

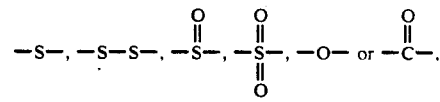

each X is independently hydrogen, chlorine, bromine, fluorine or an alkyl groups of 1-4 carbons or an aryl group of 6-8 carbons and n is 0 to 1.

4. The method of claim 3 wherein the organobishydroxy compound is bisphenol A.

5. The method of claim 1 wherein the polycarbonate polymerization reaction mixture contains an organic chloroformate oligomer.

6. The method of claim 5 wherein the organic chloroformate oligomer is a mixture represented by the formulas I, II and III:

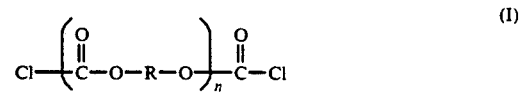
(I)

-continued

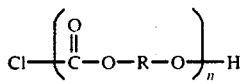  (II)

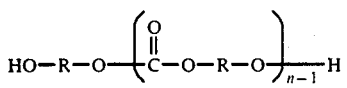  (III)

wherein R is a divalent aromatic radical and n is at least 1 and the number average for n is less than 10.

7. The method of claim 1 wherein the wavelength of the radiation is in the range from about 300 nm. to about 3,000 nm.

8. The method of claim 1 wherein the radiation is visible white light.

9. The method of claim 1 wherein the endpoint is the stoichiometric endpoint.

10. The method of claim 9 wherein the threshold proportion is determined by correlating a series of said proportions with corresponding concentrations of aromatic hydroxyl endgroups.

11. The method of claim 1 wherein the endpoint is an off-stoichiometric endpoint.

12. The method of claim 11 wherein the threshold proportion is determined by correlating a series of said proportions with corresponding concentrations of aromatic hydroxyl endgroups.

13. The method of claim 1 wherein said proportion is monitored by detecting transmitted light.

14. The method of claim 13 wherein said transmitted light is monitored by a photoconductive cell.

15. The method of claim 1 wherein the water-insoluble organic phase comprises a halogenated hydrocarbon.

16. The method of claim 15 wherein the organic phase is methylene chloride.

17. The method of claim 1 wherein the interfacial polycarbonate catalyst is a tertiary amine.

18. The method of claim 17 wherein the condensation catalyst is triethylamine.

19. The method of claim 1 wherein a chainstopper is employed.

20. The method of claim 16 wherein the chainstopper is phenol or a substituted phenol.

* * * * *